United States Patent [19]
Gamble et al.

[11] Patent Number: 6,001,309
[45] Date of Patent: Dec. 14, 1999

[54] JET DROPLET DEVICE

[75] Inventors: Ronald C. Gamble, Altadena; Thomas P. Theriault, Manhattan Beach; John Baldeschwieler, Pasadena, all of Calif.

[73] Assignee: Incyte Pharmaceuticals, Inc., Palo Alto, Calif.

[21] Appl. No.: 09/079,871

[22] Filed: May 15, 1998

Related U.S. Application Data

[62] Division of application No. 08/649,535, May 17, 1996.

[51] Int. Cl.$^6$ ........................................................ B01L 3/02
[52] U.S. Cl. .............................. 422/100; 347/19; 347/85; 422/64; 422/65; 435/286.4; 435/287.3; 436/518
[58] Field of Search ................................ 422/100, 64, 65; 347/19, 85; 436/518; 435/286.4, 287.3

[56] References Cited

U.S. PATENT DOCUMENTS

| | | |
|---|---|---|
| 4,413,275 | 11/1983 | Horiuchi et al. |
| 4,562,157 | 12/1985 | Lowe et al. |
| 4,866,166 | 9/1989 | Wigler . |
| 4,877,745 | 10/1989 | Hayes et al . |
| 5,073,495 | 12/1991 | Anderson . |
| 5,108,926 | 4/1992 | Klebe . |
| 5,143,854 | 9/1992 | Pirrung et al. |
| 5,202,231 | 4/1993 | Drmanac et al. |
| 5,202,418 | 4/1993 | Lebl et al. |
| 5,252,743 | 10/1993 | Barrett et al. |
| 5,338,688 | 8/1994 | Deeg et al. |
| 5,338,831 | 8/1994 | Lebl et al. |
| 5,342,585 | 8/1994 | Lebl et al. |
| 5,384,261 | 1/1995 | Winkler et al. |
| 5,391,667 | 2/1995 | Dellinger . |
| 5,403,708 | 4/1995 | Brennan et al. |
| 5,412,087 | 5/1995 | McGall et al . |
| 5,508,200 | 4/1996 | Tiffany et al. |
| 5,601,980 | 2/1997 | Gordon et al. |
| 5,658,802 | 8/1997 | Hayes et al. |
| 5,731,826 | 3/1998 | Hirano . |
| 5,763,278 | 6/1998 | Sickinger et al. |
| 5,785,926 | 7/1998 | Seubert et al. |

FOREIGN PATENT DOCUMENTS

| | | |
|---|---|---|
| 0 138 075 | 4/1985 | European Pat. Off. . |
| 0 392 546 | 10/1990 | European Pat. Off. . |
| 0260965 | 3/1998 | European Pat. Off. . |
| WO 87/02133 | 4/1987 | WIPO . |
| WO 88/02019 | 3/1988 | WIPO . |
| WO 89/10977 | 11/1989 | WIPO . |
| WO 90/00626 | 1/1990 | WIPO . |
| WO 90/03382 | 4/1990 | WIPO . |
| WO 92/10588 | 6/1992 | WIPO . |
| WO 93/04204 | 3/1993 | WIPO . |
| WO 93/09668 | 5/1993 | WIPO . |
| WO 93/17126 | 9/1993 | WIPO . |
| WO 93/22480 | 11/1993 | WIPO . |
| WO 94/27719 | 12/1994 | WIPO . |
| WO 95/04160 | 2/1995 | WIPO . |
| WO 95/18868 | 7/1995 | WIPO . |
| WO 95/35505 | 12/1995 | WIPO . |

OTHER PUBLICATIONS

Southern et al., "Analyzing and Comparing Nucleic Acid Sequences by Hybridization to Arrays of Oligonucleotides: Evaluation Using Experimental Models", *Genomics*, 13: 1008–1017 (1992).

Lipshutz, "Likelihood DNA Sequencing by Hybridization", *J. of Ciomolecular Structure & Dynamics*, 11: 637–653 (1993).

*Primary Examiner*—Jan Ludlow
*Attorney, Agent, or Firm*—Incyte Pharmaceuticals, Inc.

[57] ABSTRACT

Devices and methods are provided for precise reduction of arrays of microspots. A pulse jetting device is employed having a capillary of micron dimensions, with a portion of the capillary proximal to the jetting orifice circumferentially surrounded by a piezoelectric transducer. By appropriate design of the capillary, orifice and piezoelectric transducer, droplets can be formed on a surface, separated by as little as 80 microns center-to-center, and having at least about a 15 micron spacing at the border. The subject substrate arrays can be used for providing miniaturized arrays of reagents, such as nucleic acids, for detecting the presence of homologous sequences in a sample.

14 Claims, 7 Drawing Sheets

JET DROPLET DEVICE

This application is a divisional application of U.S. application Ser. No. 08/649,535, filed May 17, 1996.

BACKGROUND

Miniaturization has become a major goal for a wide variety of purposes. An area of great activity has been the synthesis of oligomers, both oligonucleotides and oligopeptides. By having large arrays of different oligomers, one can screen compositions in a variety of ways. For example, with oligonucleotides, one can screen a composition for homologous sequences or complementary sequences. In this way, one can determine the presence of homologous sequences, one can sequence a nucleic acid sequence, and one can identify a pattern of binding which can be associated with an individual, such as a strain, person, plant, or the like. With oligopeptides, there is the opportunity to screen for specific binding proteins which have high affinities to a particular oligopeptide.

The interest in large arrays has been furthered by the continued efforts to improve labels. Thus, as fluorescent and chemiluminescent labels have been developed which provide for high sensitivity, one has the opportunity to detect increasingly smaller amounts of materials. Also, in many instances, one may only have a very small amount of material in a sample, particularly in a complex mixture of materials, so that it becomes desirable to have a small amount of a highly concentrated reagent, so that the complementary member is also highly concentrated.

In providing for large arrays of small dots, there are a number of considerations. The dots should be substantially reproducible in size, particularly if one wishes to quantitate an analyte. Secondly, in the past, it was frequently found that the droplet was associated with satellite droplets, which separated from the main spot and could contaminate other spots, confusing the assay. Third, the device employed, if it is to have commercial acceptance, must be readily filled, be reliable in producing droplets, be easily cleaned, and be reproducible in performance.

U.S. Pat. No. 4,877,745 describes a piezo jet for providing small droplets to produce an assay array. The operation of the device is not particularly convenient, and the droplets are reported to be in the range of 100 pL to 1 $\mu$L with the size of the spot made by each droplet being approximately 0.001–0.012 inches in diameter. Schena et al., Science (1995) 270:467–470, describe the preparation of dot arrays for analysis.

SUMMARY OF THE INVENTION

Systems are provided for delivery of small volumes of solutions in a precise manner to provide a microsized spot. For providing for a predefined distribution of solution spots on a surface, the system comprises an array of microdroplet producing devices, means for filling and cleaning the microdroplet devices at a storage station, means for moving the microdroplet producing devices from the storage station to a position in relation to a surface onto which the microdroplets are deposited to provide spots at precise sites on a surface, and means for moving the microdroplet devices and surface in relation one to another. Groups of microdroplet producing devices are provided for directing droplets in a precise array onto a substrate. The microdroplet device uses a capillary with an energy transducer, which imparts energy to the solution in the capillary. The energy transducer may be a concentrically placed piezoelectric transducer around the capillary proximal to the dispensing end or a heating element. In addition to the capillary and transducer are a sample receptacle in liquid transfer relationship with the sample receiving end of the capillary, from which the liquid fills the capillary, and a housing. Microdroplets of less than about 500 pL can be reliably dispensed providing arrays of 10,000 spots in one square $cm^2$. With a polar medium, a dispenser having a hydrophobic surface is employed, placed in close proximity to the receiving end of the capillary whereby the polar medium fills the capillary by capillary action. By activation of the transducer, the fluid in the region of the capillary outside the transducer is reliably dispensed at a high rate to provide the desired array. By appropriate choice of a substrate, various reagents may be bound to the surface of the substrate to provide for a stable assay array. Assay arrays may be used for detecting specific binding of complementary members.

DESCRIPTION OF THE SPECIFIC EMBODIMENTS

Figure 1:
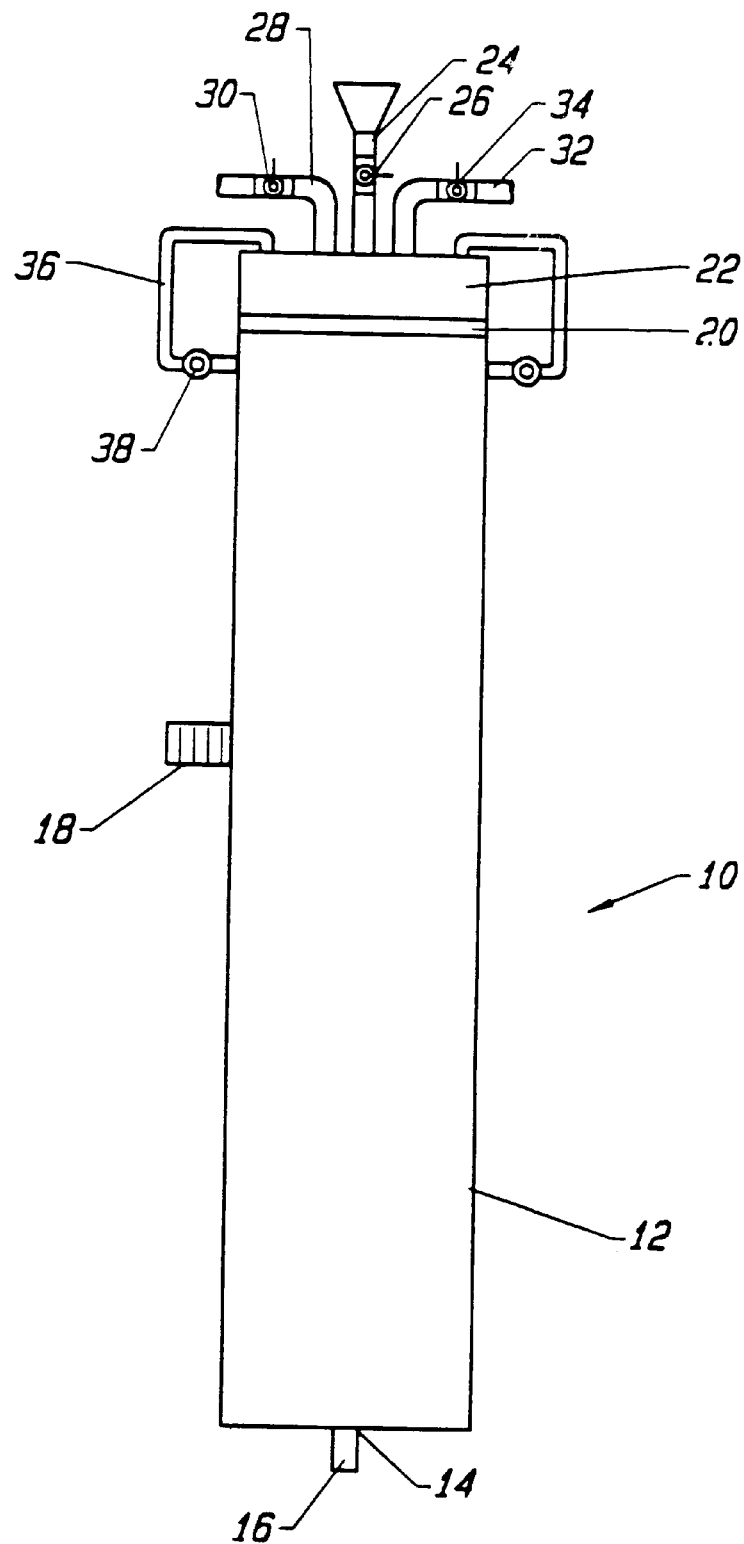
FIG. 1 is a perspective elevational view of the device.

The subject invention provides a system for precisely placing microsized droplets on a surface as microsized non-overlapping spots in a closely packed array. The system provides for movement of fluid pulse jetting dispensers such as piezoelectric and thermal dispensers from a storage bank to the dispensing site for directing droplets to a predetermined site on a surface, and returning the dispensers to the storage bank upon completion of their dispensing function. Alternatively, the dispensers may be disposable. At the storage bank, the dispensers may be fitted with a manifold by which the dispensers are cleaned and filled with the solution for dispensing. The system provides for producing large numbers of arrays of small spots in a confined space. The system comprises a plurality of pulse jet dispensers, a storage bank for cleaning and filling the dispensers, means for moving the dispensers from an inactive position in the storage bank to an active position for dispensing droplets onto a surface and returning the dispenser to the storage bank when its role is completed, and means for moving the surface and the dispensers in relation to each other. Also, while the dispensers are in the storage bank, the dispensers can be cleaned by washing and filled with solution from above, using capillary action to fill the capillary of the dispenser.

Where the dispensers are disposable, the storage bank will have the dispensers loaded with sample, particularly having groups of the dispensers, where each of the dispensers may have the same or different medium for dispensing, in a predetermined arrangement of media. When moved into dispensing position, the group will provide an array of spots on the surface in accordance with a prearranged organization.

For non-disposable dispensers, the device provides for introduction of a sample solution into a sample receptacle, which in the case of a polar solution, is not wetted by the sample. The receptacle port has a tight fit with the receiving port of the capillary, so that for a polar medium, contact with the sample results in rapid filling of the capillary without any positive force other than capillary action. A manifold with a valved pressure system comprising a reduced pressure supply conduit is provided which allows for drawing up solution for cleaning of the capillary after use; and a valved elevated pressure system including an elevated pressure supply conduit for blowing out remaining sample solution, cleaning solution or other solutions from the capillary. In view of the very small volume of individual droplets, only a small volume is required to fill the capillary and produce a large array of spots.

For protecting the capillary, the device includes a capillary casing or support for holding the capillary in position and maintaining the capillary in a housing, which casing is at the capillary region proximal to the sample receiving port. The casing fills the space between the capillary and inner wall of the housing, desirably being threaded into the housing. Various transducers for droplet formation may be used, where such transducers are commercially available. These transducers include piezoelectric transducers and heat transducers (bubble jets).

A piezoelectric transducer is provided which concentrically surrounds a region of the capillary proximal to the orifice. Wires from the piezoelectric transducer can be directed upward into or at the surface of the casing and extend outside the casing for electrical contact with the electrical activation source. The capillary has a flat bottom, where the outer diameter remains substantially constant, while the internal diameter is substantially narrowed to provide the desired sized orifice. The bubble jet has a distal fill opening connected to a heater channel in which is a resistive heater, the channel terminating in an orifice.

The fluid jetting device can be used individually or in combinations of a plurality of jetting devices in one or more defined groups, where each of the devices may have a different sample. With combinations, one could have assembly lines of jetting devices, where each of the devices can dispense its reagent at a precise position on the substrate to provide the array, or one may robotically move the jetting devices to different positions in relation to the substrate, or move the substrate in relation to the jetting device, or combinations thereof. Since the jetting device may be much larger than the spot which it creates, groups of jetting devices may be fashioned, where each device group provides for a portion of the total substrate array. The jetting devices may be placed at an angle to substrate to increase the number of jetting devices in each device array and to control the size of the spot, where the spot would be elongated due to movement of the surface in relation to the dispenser. One may also use a plurality of individual jetting devices, where the individual jetting devices are selected and moved into position robotically, so that one may elect a particular jetting device from a bank of devices to produce a variety of substrate array spots.

The entire system may be controlled using a computer program to provide for the automatic cleaning and filling of jetting dispensers, selection of dispensers from the storage bank for movement from the storage bank to a dispensing position in relation to the surface, organizing the array of dispensers in relation to the surface, controlling the movement of the dispensers and/or surface in relation to each other, controlling the droplet dispensing to provide the desired array of spots on the surface and returning dispensers to the storage bank when their function is terminated. Movement may be in the X-Y direction or circular angular direction or a combination of both.

Groups of dispensers may be combined in a block and wired to a connector, so that each dispenser is wired to a specific position of the connector. The connector may be a male or female connector and when plugged into a reciprocal connector will provide a circuit, which may be computer controlled, where all of the dispensers may dispense simultaneously or in accordance with a predetermined program. One may provide for a plurality of groups of dispensers which may be positioned over the surface to fire simultaneously or consecutively to define the desired array pattern.

The subject systems may be used in a variety of situations to produce arrays, feed sample or reagent, or the like. The solutions may contain a variety of components, including individual compounds, oligomers and polymers, naturally occurring or synthetic, chemically reactive or unreactive, or the like. The subject systems may be used to synthesize oligomers, such as poly(amino acids), where the individual amino acids may be naturally occurring or synthetic. Instead of amino acids, naturally occurring or synthetic nucleotides, monosaccharides, or other reactive compounds, may be used to synthesize oligomers or new compounds. In this way combinatorial approaches may be used to prepare an array of different compounds at a plurality of sites in the array. Alternatively, one may add compounds, including oligomers, to specific sites for screening purposes, diagnostic purposes, or the like. The subject devices may also be used in screening for a particular activity of interest, such as ligand-receptor binding, hybridization of complementary nucleic acids, agonist or antagonist activity, or a physical characteristic, such as fluorescence, luminescence, light absorption, etc. For screening assays, particularly in assays in which a second sample comprising one or more reagents of the assays is contacted with a first sample comprising one or more reagents of the assay, a first sample comprising one or more of the members of an assay, e.g. an analyte, oligonucleotide probe etc., may be pulse jetted with the device to produce one or more, usually an array of, spots of first sample on a surface. A second sample comprising additional assay members, e.g. receptor, etc., may be pulse jetted onto the array of spots of first sample, followed by a detection step for the presence or absence of the activity of interest, e.g. binding, hybridization and the like. Alternatively, the first sample may be present on a substrate as a continuous layer or film, as a preformed array of discrete spots, etc. The detection step may, if necessary, include one or more washing as well as any other steps required for detection.

The surface on which the droplets are dispensed may take many forms, depending on the nature of the material that is being dispensed and the purpose of the array. The surface may be chemically reactive or physically active, e.g. binding, so that the component(s) of the droplets become non-diffusibly bound to the surface, e.g. through electrostatic attraction, covalent bonding and the like. Where one is synthesizing a compound, e.g. an oligomer, there will usually be an initial precursor bonded to the surface to provide a site for reaction. The precursor may be bonded to the surface through a scissile bond, so that the product may be released from the surface. By having photolytically cleavable bonds, one can individually release the molecules from a specific site, as appropriate. The approaches used for combinatorial chemistry are applicable to the use of the subject systems. In addition, in diagnostic applications, one may dispense sample, reagents, or the like. Particularly, one need not bathe the array with a reagent, but can apply the same or different reagents at different sites to perform a plurality of the same or different assays. Thus, one can design assays in which an array of droplets or spots comprising a first assay reagent, e.g. either a known or unknown in the assay, is prepared on a substrate and then a second assay reagent(s) is introduced in the form of droplets or spots onto the previously deposited droplet members of the array, where the assay may be carried out humid conditions, as necessary. For example, one could coat the surface with the sample or dispense the sample as individual droplets to form an array of sample. Different reagents could then be dispensed at different sites, with some redundancy for accuracy, so that the sample could be screened for a plurality of different indications. As illustrative, one could coat the surface with DNA from a lysed cellular sample and then dispense droplets of labeled fragments of different DNA sequences under hybridizing conditions. By observing the pattern of the sample remaining following removal of unbound labeled fragments, one may define the individual for forensic purposes, determine the presence of a pathogen, identify a cell type, identify neoplastic cells, provide a prognosis, and the like. Where one is interested in screening for physiological activity, one can dispense the same or different receptors at each site having different compounds and determine the binding of the receptor at the individual sites. Based on the pattern of binding, one can obtain a structure-activity profile to design additional compounds to optimize the binding affinity.

Depending on the nature of the medium, mixed solvents may be desirable or required. In the case of DNA, addition of dimethylsulfoxide ranging from 1 to 100%, preferably 30 to 70%, would be desirable to cut the aqueous buffered DNA solution. This improves the jetting by forming more uniform spots and reducing the rate of solvent evaporation, which allows for more uniform coverage around the edge of the spot as well as in the center. Where the DNA solution is too viscous, other solvents may be used to provide the desired viscosity as appropriate for the jetting dispenser. Convenient solvents, which may be used with DNA samples or nucleotide monomers for synthesis, e.g. phosphoramidites, include acetonitrile, dimethylformamide, trimethylphosphate, etc. generally in from about 1–20 volume %, while lower alkanols, e.g. ethanol, may be used in the 1–10% range, depending on the salt concentration.

For further understanding of the invention, the drawings will now be considered. In FIG. 1, the device 10 has an outer housing 12 which encompasses the capillary assembly and provides protection and ease of handling of the device 10. While the housing 12 may be of any shape, the housing 12 is conveniently cylindrical, so that commercially available tubing can be used and the housing 12 may be machined to provide for assembly of the various parts. The housing 12 has a symmetrically situated opening 14 through which the capillary 16 extends. A threaded side bracket 18 is provided for attachment of the housing 12 to a support. Any convenient means may be employed for attaching the housing to a holder, which will allow for positioning the device, and as appropriate, the movement of the device. At the top of the housing is gasket 20, which provides for an airtight seal. Also shown is the lid or cover 22 employed during cleaning and filling of the device. During cleaning, cover 22 is used for sealing the region above the capillary 16. Included in the cover 22 is first conduit 24 for cleaning solvent addition, where the conduit can be closed, conveniently with valve 26, when the system needs to be evacuated or pressurized; second conduit 28 for connecting to a vacuum source, not shown, having valve 30 for closing the system from the vacuum; and third conduit 32 for introducing gas pressure, which is controlled by valve 34. The use of the various conduits will be described subsequently. Finally, for further assurance of hermetic sealing while the cleaning and filling cover is in place, one may have clips 36 mounted on hinge pins 38 for locking the cover 22 into position and holding the cover 22 in an airtight sealed relationship with gasket 20.

Figure 2:
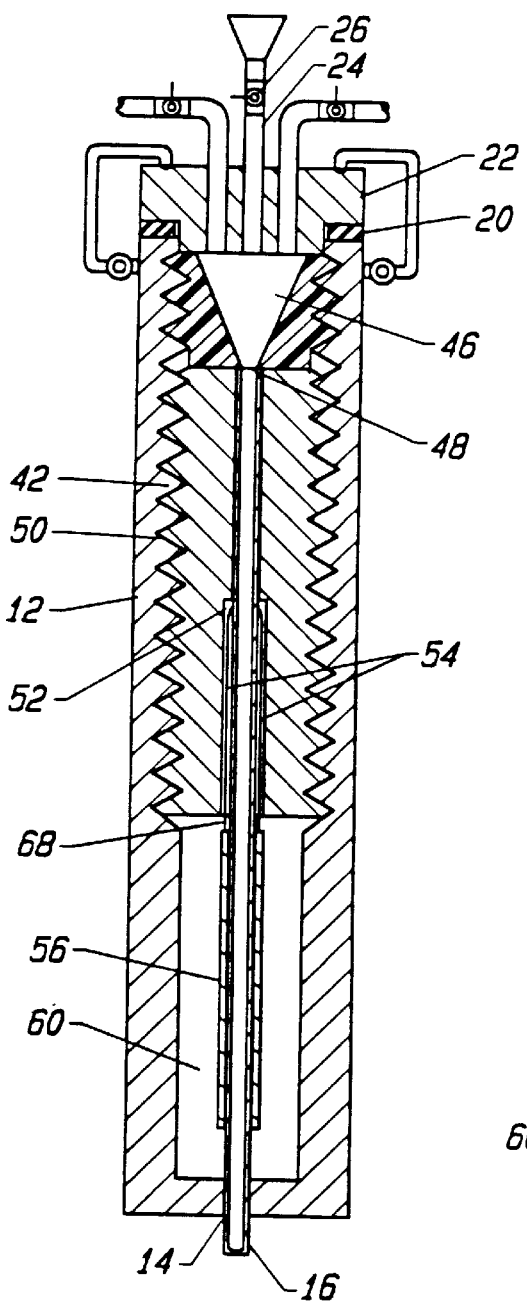
FIG. 2 is a cross-sectional elevational view of the capillary holder.

In FIG. 2 is shown a cross section of the internal portion of the housing 12.

The capillary 16 extends through opening 14 in housing 12. The inside of housing 12 is threaded with threads 42 extending about two-thirds the distance of the housing.

Cover 22 is adjacent to a threaded tube 44 extending into the housing 12, where it can be clamped into position to provide for an airtight relationship with gasket 20. The threaded tube 44 can be made of a hydrophobic material, such as nylon, which also provides for a tight seal with the threads and can serve to lock the capillary casing 50 in the housing 12. The threaded tube 44 has a conical receptacle 46 for receiving the sample. After cleaning, the cover 22 is removed exposing the conical receptacle 46, which is then available for receiving sample. The conical receptacle 46 has port 48, which meets the capillary so as to form a tight seal, whereby the sample can touch the capillary 16 and by surface tension the sample can move the length of the capillary 16 to fill the capillary.

The capillary 16 fits snugly into threaded casing 50 so as to be supported for a substantial portion of its length. Threaded casing 50 has notch 52 which extends downward through threaded casing 50 to receive wires 54 for activating the transducer 56. The capillary 16 and piezoelectric transducer 56 extend through cavity 60 where they are protected by housing 12. The capillary 16 may be affixed to the threaded casing 50 by any convenient cement, e.g. epoxy.

The threaded casing 50 may be a monolithic piece or may be prepared in two or more sections. For example one might have a lower section with a vertical notch 52 for the wires, a central section which includes a channel for accessibility to the wires, and an upper section to complete the casing and completely enclose the capillary 16. The particular form which the casing takes will depend on the manner of assembly, ease of assembly of the capillary 16 in the casing 50, ease of cementing the capillary 16 to the casing 50, and the like.

The device is readily assembled by introducing the capillary 16 into the casing 50 and cementing the capillary 16 into the casing 50. At the top surface of the casing 50, the capillary 16 is polished, so as to have a smooth surface and be able to form a tight liquid transfer relationship with the receptacle port 48

Figure 3:
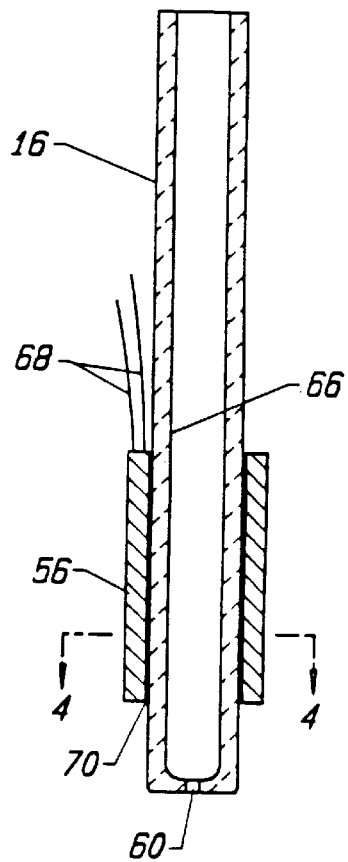
FIG. 3 is a perspective elevational view of the capillary and piezoelectric transducer.

In FIG. 3, a capillary 16 is shown without the casing 50 but having the piezoelectric transducer 56 mounted on the capillary 16. The piezoelectric transducer 56 is proximal to the orifice 60 leaving about one-half to two-thirds of the length of the capillary 16 exposed above the transducer 56.

Figure 5:
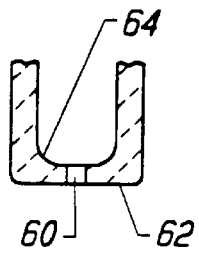
FIG. 5 is an expanded view of the orifice region of the capillary.

The transducer 56 has a very narrow tolerance with the capillary, usually less than about 0.001 inch and is also affixed to the capillary with a cement. Conveniently, a ceramic piezoelectric tube may be employed, such as PZT-5a, available from Vernitron Piezoelectric Division. The characteristics of the piezoelectric transducer may be found in the companies manual entitled, Piezoelectric Technology, Data for Designers, 1990. The walls of the capillary 16 are quite thin, so that they can move with the expansion and contraction of the piezoelectric transducer 56. As shown in FIG. 5, the capillary 16 narrows to a narrow orifice 60 with a flat bottom 62. The rounded internal bottom of the capillary 64 provides for a rapid reduction in diameter from the inner diameter of the capillary 16 to the diameter of the orifice 60. This can be achieved by heating the capillary and allowing the glass or quartz to collapse to form the orifice.

Figure 4:
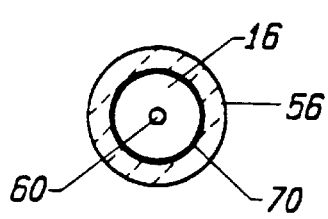
FIG. 4 is a cross-sectional view of the capillary and piezoelectric transducer looking toward the orifice.

Leads 68 are provided for providing electrical contact with the piezoelectric transducer. Cement 70 is introduced between the transducer 56 and the capillary 16, so as to maintain tight linkage between the transducer 56 and the capillary 16. In FIG. 4, we see the piezoelectric transducer 56 surrounding and sealed to the capillary 16 by a cement 70.

The dimensions of the capillary, orifice, and transducer are important to the successful operation of the subject liquid pulse jetting device. The orifice region has a fairly constant outer diameter, which is achieved by heating a capillary tube so that the glass softens and fills the inner portion of the capillary to provide the desired orifice diameter. The orifice diameter will generally vary in the range of about 10 to 100 $\mu$, depending upon the surface tension of the fluid employed. With lower surface tensions, one can reduce the size of the orifice. Generally, for water, without additives for reduced surface tension, the orifice will be in the range from about 40 to 80 microns. With additives which reduce surface tension, the orifice is desirably in the range of about 10 to 50 microns in diameter.

The capillary length will generally be in the range of about 1.5 to 4, usually about 2 to 3.5 cm. The orifice region extending from the piezoelectric transducer will generally be about 5 to 15% of the length of the capillary, more usually about 5 to 10% of the length. The transducer will usually cover about 20 to 40%, more usually from about 25 to 35% of the length of the capillary. The region above the transducer will be at least 40% of the length of the capillary and may be up to 75%, usually not more than about 60%. At least 80%, more usually at least 90%, and generally not more than about 99% of the length of the capillary will be enclosed by the housing 12.

The thickness of the walls of the capillary will generally be between about 0.10 to 0.40 mm, preferably about 0.25 mm, while the capillary inner diameter will be at least about 0.10 mm and not more than about 0.50 mm, usually not more than about 0.40 mm, preferably about 0.25 mm. It is found that the liquid capacity of the capillary coming within these dimensions provides for 10,000 or more spots, before requiring cleaning and refilling, where the volume of the capillary will typically range from about 1 to 10 $\mu$l.

In fabricating the fluid jetting dispenser, the preformed capillary is passed through the piezoelectric transducer which has a small amount of a cement on its inner surface. The tolerance between the outer surface of the capillary and the inner surface of the transducer should be very small, preferably less than about 1 mm. The cement dries and provides for a strong bond between the inner wall of the transducer and the outer wall of the capillary, so that the transducer and wall move in unison. The capillary may now be introduced through the threaded casing until the capillary extends the length of the casing. The end of the capillary may extend beyond the length of the casing and be cut and polished to provide a smooth surface. Alternatively, the capillary may be precut and polished, and carefully fitted into the casing so as to terminate at the surface of the casing. The particular manner in which the capillary and casing are joined and fitted will be primarily a matter of production. The wires for the transducer may then be passed through the notch and bore and may be accessed through an opening in the housing. Alternatively, the wires may be soldered to connectors on the casing at the bore site, so that when threaded into the housing, the connectors will make connection to connectors in the housing for access to the electrical activator and regulator.

The capillary and casing may then be threaded into the housing, so that the capillary extends beyond the opening of the housing and is firmly positioned. During the cleaning operation, the cover is then threaded into the housing, firmly locking the capillary and holder into position, so as to provide a stable structure. The cover may have the conduits integrally as a part of the cover. Alternatively, the cover may have a central opening over which a utility lid may be placed, which lid may also include a gasket which seals the lid to the cover. The utility lid would have the necessary conduits and could be moved from a position where it is engaged with the housing to a position where it is disengaged. Alternatively, the cover may have a relatively large opening, so that a plug comprising the various conduits, may be inserted into the opening of the cover. The plug may be part of a manifold of a plurality of plugs, which can be fitted into a plurality of openings, so that a plurality of capillaries may be simultaneously processed, such as filling and cleaning at the same time. Capillaries may be washed and then stored for filling at a subsequent time or filled promptly after washing. Which expedient is employed will depend to some degree on the manner in which the device is employed. Where the device is at a fixed station, fixed connection of the conduits to the device would be convenient. However, where the device is moved during operation from a banked or reserve position to an active position or is moved for cleaning, it will be expedient to have the lid or plug engaged only during the cleaning operation.

If desired, a heating element may be provided in the device for warming the capillary and reducing the viscosity of the fluid in the capillary. The heating device may be wrapped around the housing, fitted into the capillary casing, or the like. The particular manner in which heat may be transferred to the capillary is not critical and various conventional design parameters may be employed.

Instead of a piezoelectric jet dispenser a bubble jet may be used which employs a heating element to produce droplets. See, Asai, et al., Japanese Journal of Applied Physics (1987) 26:1794–1801. The bubble jets are about 30 $\mu$m wide and can be arranged in clusters of at least 64 jets to provide clusters of 14 dots per mm. An exemplary bubble jet tube would have a length of about 500 to 600 $\mu$m, an inner diameter of about 60 $\mu$m and a nozzle about 46 $\mu$m, with the heating element placed about 190 $\mu$m from the nozzle. The heating element has a plurality of layers, using 0.5 $\mu$m aluminum electrodes, with coatings of $SiO_2$ (5 $\mu$m and 1.9 $\mu$m), $HfB_2$ resistor (0.13 $\mu$m), $Ta_2O_5$ passivation layer (1.9 $\mu$m), Ta protection layer (0.55 $\mu$m), and 550 $\mu$m of Si substrate. The length of the heater is about 150 $\mu$m.

Figure 8:
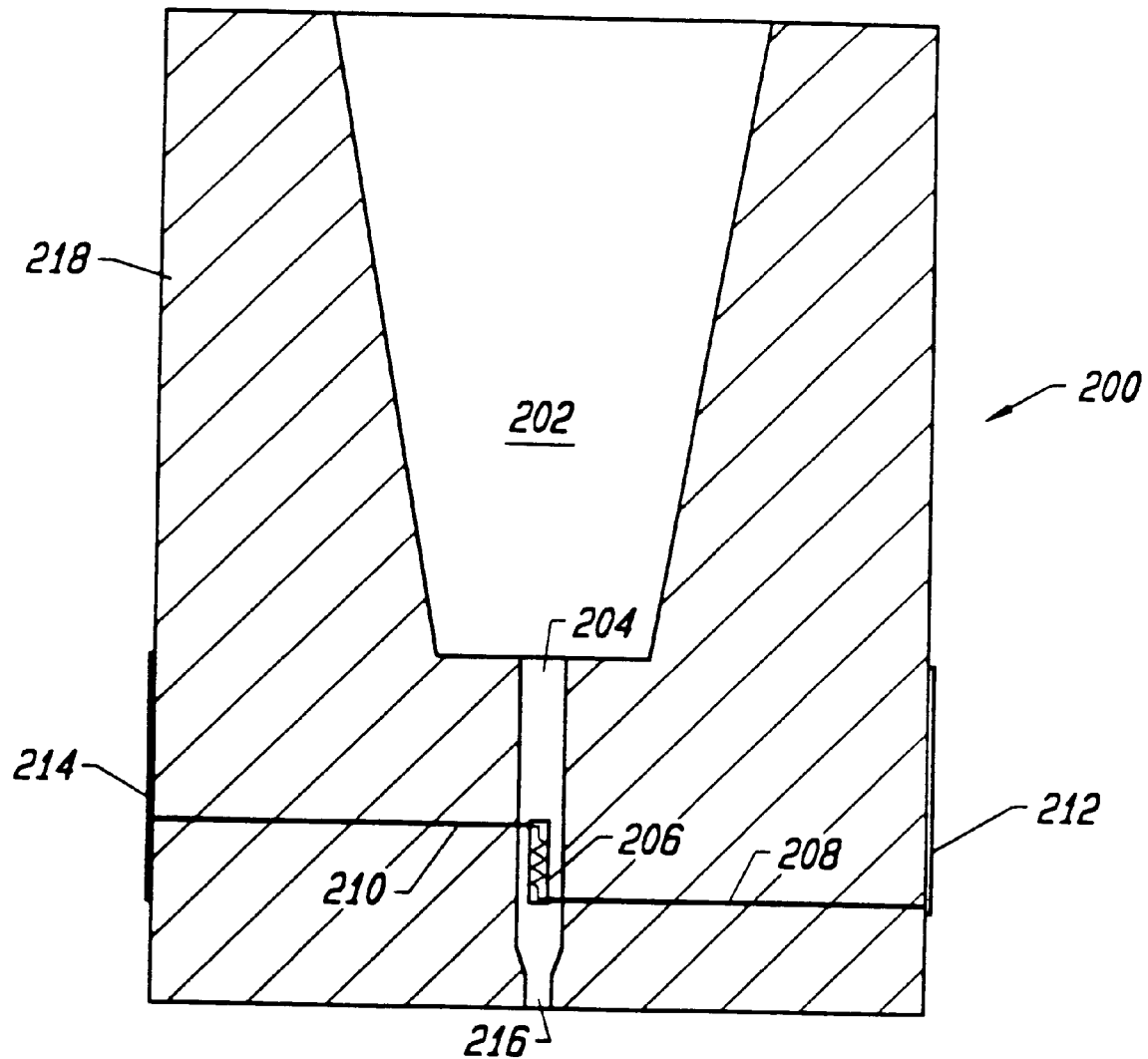
FIG. 8 is a diagrammatic elevational view of a bubble jet for use in the subject invention.

In FIG. 8, the bubble jet 200, has V-shaped reservoir or sample receptacle 202 for distal filling, much in the same manner as the piezoelectric jetting device, where the volume of the reservoir may range from about 0.2 to 20 μl, and will usually range from about 0.5 to 5 μl. The reservoir 202 is connected to the heater channel 204. Resistive heater 206 is connected by means of conductive lines 208 and 210 to electrical contacts 212 and 214, respectively. The heater channel 204 terminates in orifice 216. The capillary wall 218 can be readily formed from any convenient material and the necessary electrical connections and heater positioned in or on the wall 218 and in the channel 204 in accordance with known procedures. Bubble jets are commercially available and may be modified to provide for top loading of sample by providing for the reservoir 202.

Groups of jets may be positioned in storage banks above or to the side of the dispensing position. By using groups of jets, one can provide for a plurality of spots being formed simultaneously on the surface. In addition, either concurrently or consecutively, the groups may be placed in position so as to dispense droplets in an interrupted manner, providing spots at different positions in the array. The groups of jets may be positioned, so as to be displaced in relation to the surface, so that droplets will be dispensed to form spots in different patterns defining only a portion of the final array, where the different patterns will add up to all of the positions of the array. The groups may be moved in unison, as a single entity, so that a robotic arm moves a plurality of jets into position simultaneously. Depending on the movement of the jets and/or surface, the jets may be positioned at an angle to the surface to prevent elongation of the spot. The rate of relative movement and the speed of the droplet will determine the angle which is employed. For example, with a droplet speed of 3 m/sec and a speed of the surface relative to the jet of 1 m/sec, the angle will be about 20°. The distance of the jet from the surface may be varied, generally being at least about 0.1 mm and not more than 0.5 mm, usually not more than about 0.2 mm.

Figure 6:
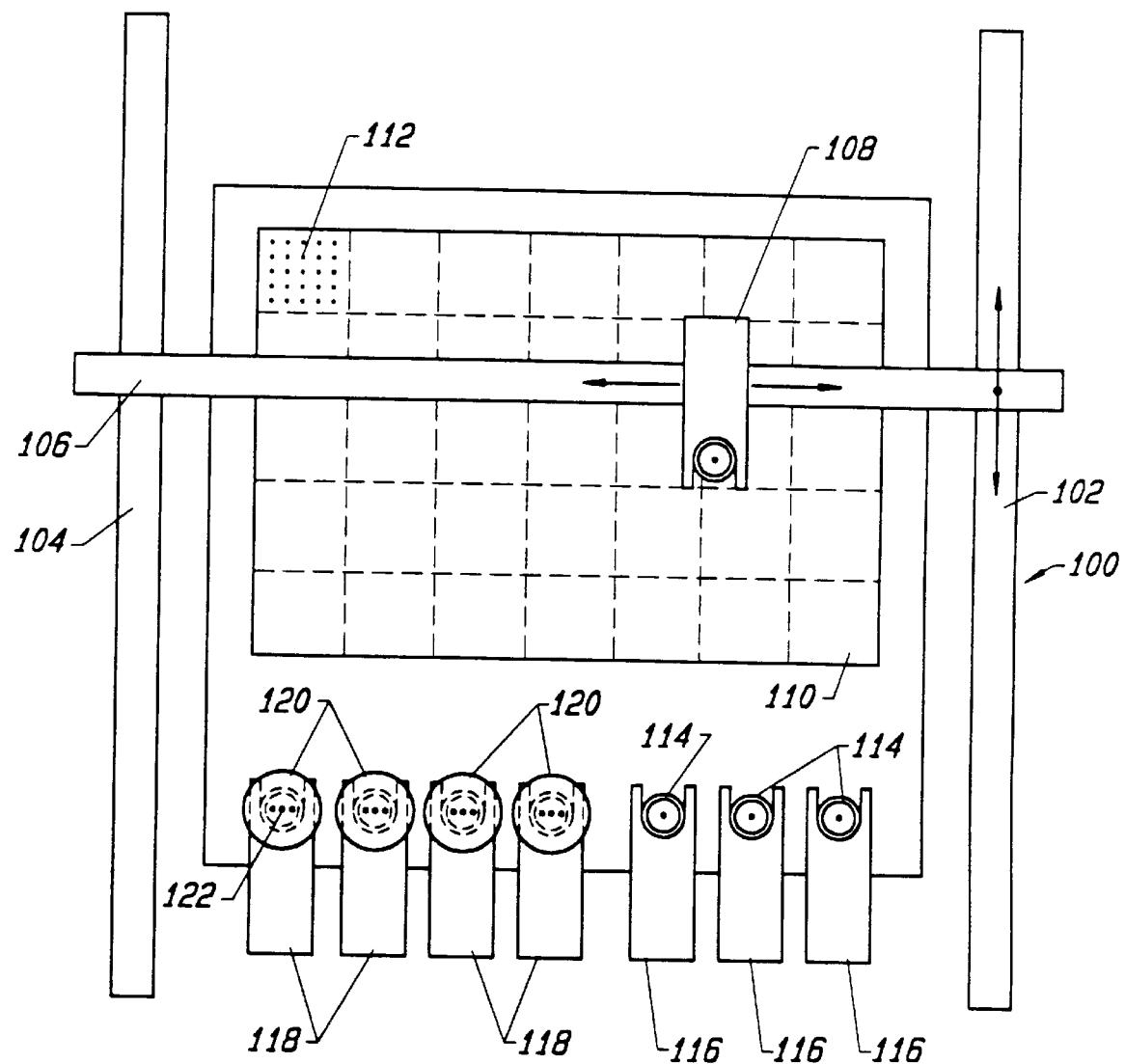
FIG. 6 is a diagrammatic view of an x-y positioner in combination with jetting devices for producing arrays.
Figure 7:
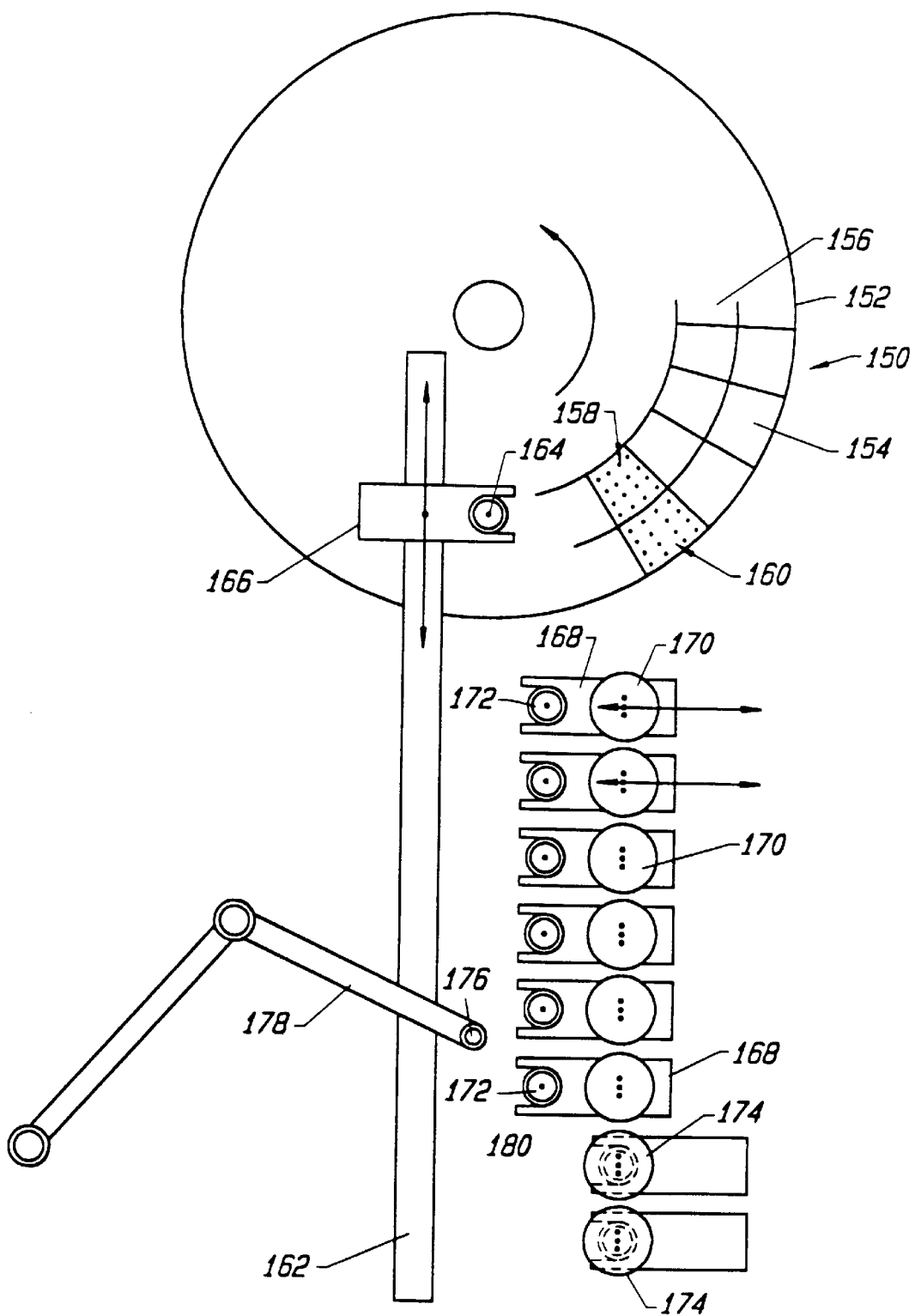
FIG. 7 is a diagrammatic view of a rotating platform in combination with jetting devices on a linear positioner for producing arrays.

To prepare the arrays, various systems may be used where the substrate and the fluid jetting device move in relation to each other. Two potential systems are shown in FIGS. 6 and 7. The first system provides for movement of the jetting devices in the x-y direction in a plane parallel to a fixed substrate. The device 100 is an x-y positioner with y-beams 102 and 104 for movement of the jetting devices in the y direction, where x-beam 106 is supported by y-beams 102 and 104, with x-beam providing movement of the fluid jetting devices in the x-direction. Resolution of the device is in the range of 1–10 microns. Movement of x-beam 106 in the y-direction with concomitant movement of the jetting device in the y-direction is controlled by a y-raster motion servomechanism, not shown, while movement of the jetting device in the x-direction is controlled by an x-raster motion servomechanism, not shown. A jetting device 108 is shown positioned on x-beam 106. The range of movement will vary with the size of the substrate, the system usually providing for an extent of movement of less than about 100 cm and usually at least about 10 cm. A substrate 110 is provided upon which the jets can deposit droplets to provide the array 112 shown in the left-hand corner of the substrate 110. A plurality of reserve jetting devices are supported by holders 116 and held in reserve. Additionally, a plurality of jetting devices are supported by holders 118, where the jetting devices are obscured by lids 120 having conduits 122 for delivery of various components to the jetting device and for cleaning. These lids may be connected into a manifold, so as to be capable of being moved simultaneously. In the operation of the x-y servomechanism, x-beam 106 can move to the bank of jetting devices retained in reserve, the operative jetting device 108 returned to the reserve bank, and a different jetting device mounted on x-beam 106. During operation, each jetting device in turn may provide for a plurality of spots of the same reagent at different sites on the substrate, so that each portion of the substrate has the same reagent at comparable places at each array. As shown in FIG. 6, substrate 110 is delineated into a number of boxes, where each box can have spots defining an array which is identical to every other box.

For x-y positioning, high speed (30 in/sec) positioners, covering 12–30 in in each dimension are available commercially (e.g. Asymtek, Carlsbad, Calif.). Repeatability is less than 2582 . Custom positioners can be fabricated on a larger scale using optically encoded feedback for positioning below 10μ. For example, a subsystem at 30 in on a side would allow over 1200 arrays to be fabricated at one time. (This is calculated by allocating 1.5 cm on edge for 1×1 cm active array.) Rather than stopping at each position to be spotted, it is possible to synchronize the jetting pulse to the position to be jetted. The controller for the subsystem, on receiving the spot-location information from the master, would correct the timing of the jet pulse to account for the slight delay of actual arrival time of the drop onto the surface (about 60 μsec for a 180 μgap).

In FIG. 7, a comparable device is provided, but in this situation, instead of having a fixed substrate and a moveable jetting device, one has a moveable substrate and a fixed jetting device in relation to the substrate. In addition, the substrate moves in a circular direction, where there may be one or more concentric rings comprising individual arrays. The rotating substrate device 150 has a rotational platform 152 with substrate rings 154 and 156 which move concentrically. Each of the rings has a plurality of array sites 158, where the appearance of an array site is diagrammatically shown at 160. The device has a linear servomechanism 162 on which the pulse jetting device 164 in holder 166 moves. A reserve bank of pulse jetting devices 168 are available displaced from lids 170. The lids 170 may be moved into position over the reserve jetting devices 172 to fill or clean the jetting devices, as appropriate, and carry out such other steps of the process as necessary. Two lids 174 are shown above the jetting devices, indicative that the jetting devices are undergoing some processing. The capillary may be rinsed and/or washed one or more times and dried, either air dried or by passing air through the capillary by means of a vacuum or elevated pressure. A micropipetter 176 is mounted on robot arm 178 to be able to move into position over a pulse jetting device 172 to introduce samples into the device through opening 180. The jetting device will usually be in close proximity to the substrate when firing, usually in the range from about 0.1 mm to 0.5 mm.

For theta-x positioning one high speed linear translation of the sample and a moderate speed rotation of the substrate is involved. The rotation is represented by the platform 152. Linear translators are commercially available (see above), while the platform support, motor and control are customized, using equipment analogous to the control of the rotation of platters in hard disk memory used in computers. The rotational speed is limited in part by the exit velocity of the drop from the jet, typically 3 m/sec. The surface speed of the platter should be only a fraction of the exit velocity, e.g. 1 m/sec, so as to minimize elongation of the spherical drop on contact. This can be obviated in part by pointing the orifice in the direction of the platform and partly in the direction of rotation.

Figure 9:
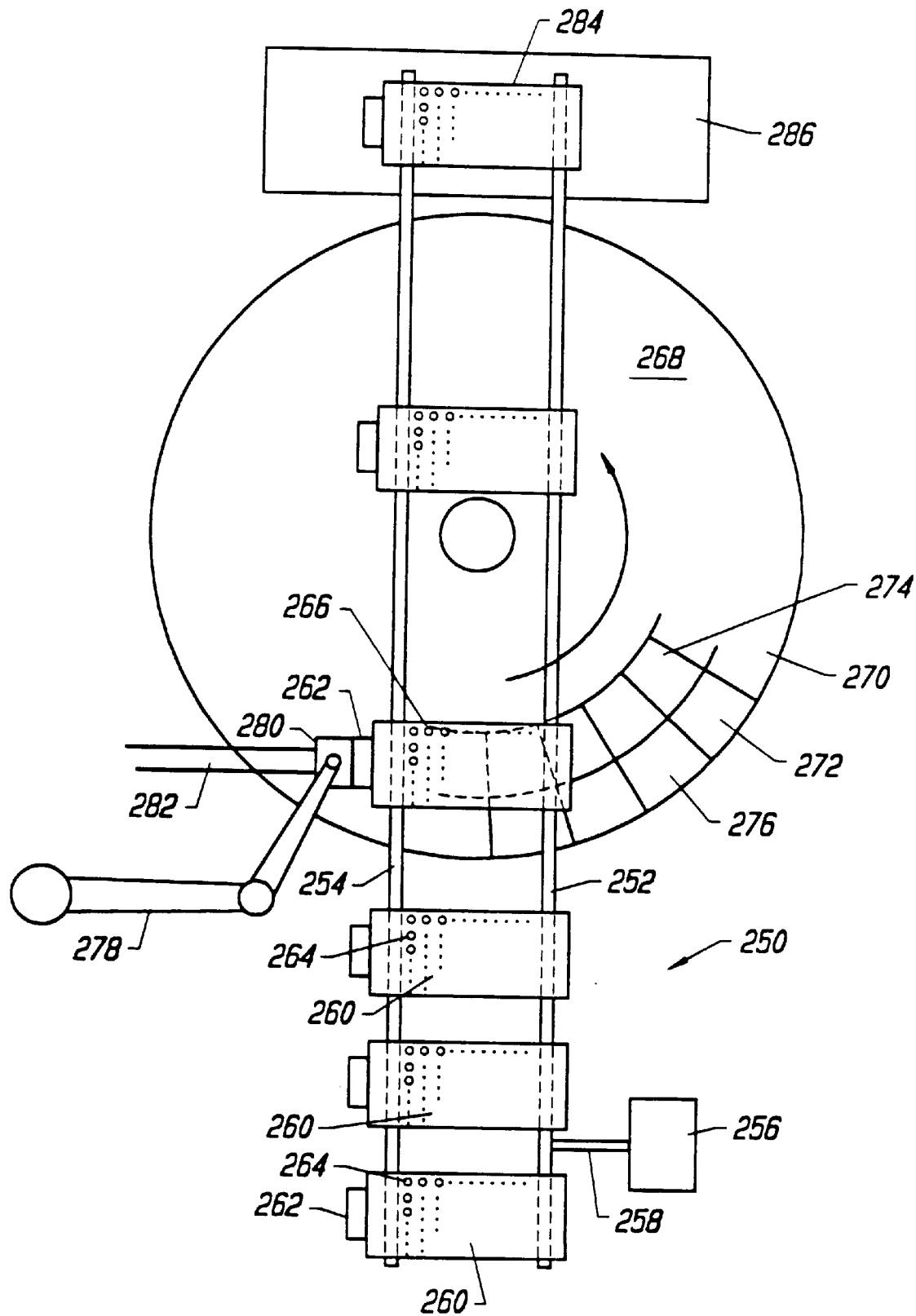
FIG. 9 is a schematic representation of a system according to the subject invention.

In FIG. 9 a different system is used, where groups of jetting devices are held together in batteries and share a common electrical connector. The system 250 has first and second rails, 252 and 254, respectively. Rail 252 has an endless belt driven by motor 256 through shaft 258. A plurality of batteries of jetting devices 260 are mounted on the rails 252 and 254, awaiting being moved into an active position for dispensing. Each battery 260 has a connector 262 with multiple leads, each lead connecting a jetting device 264 to an outside circuit for controlling the firing of the jetting device 264. When the motor 256 actuates the endless belt, the batteries 260 are moved forward, with one battery 266 being moved into an active position above the surface 268. As discussed previously in conjunction with FIG. 7, a rotational platform 270 has outer and inner substrate rings 272 and 274, respectively. Each of the rings has a plurality of array sites 276, which are indicated by the crossing lines. When the battery 266 is moved into active position above the surface 268, robot arm 278 moves the complementary connector 280 into position to engage the battery connector 262. The complementary connector 280 is connected by means of electrical conduit 282 to a circuit which may provide for simultaneous firing of all of the jets or firing of the jets at different times in accordance with a predetermined program. Once the use of the battery 266 has been terminated, robot arm 278 is actuated to disconnect connector 280 from battery connector 262. The motor 256 is actuated to move the battery 266 out of the active position and bring a new battery 260 from its storage position to the active position to replace battery 266. Battery 266 is then moved along the rails 252 and 254, ultimately coming to the terminal position 284 of the rails, where it may be deposited in collection box 286. From the collection box the battery may be reused, disposed of, or stored for subsequent use. If the battery is to be reused, it may be manually retrieved or a mechanism provided for moving the battery to a storage position, where the battery may be cleaned and replenished, as previously described.

Figure 10:
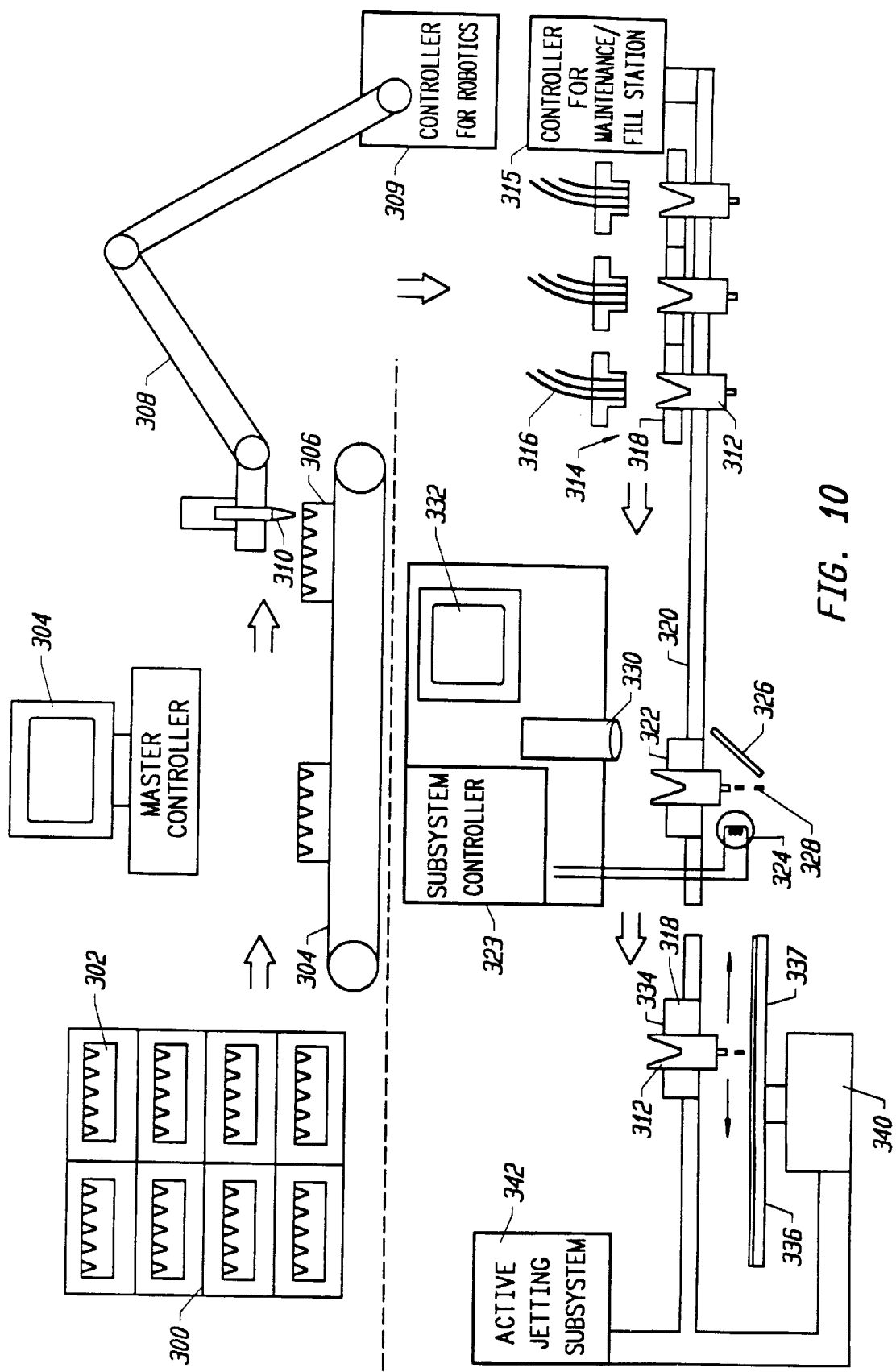
FIG. 10 is a schematic flow representation of a system for producing arrays according to the subject invention.

In FIG. 10, a storage subsystem 300 is shown as an array of racks, individually addressed under computer/bar-code control. Each bin in the rack contains an array of storage well plates 302 (e.g. 96- or 384-well microtiter plates). Samples in the storage system may be stored at an appropriate temperature for maintaining the integrity of the samples. A master controller 304 controls the system. Under computer signal, one or more micro-titer arrays 302 are conveyed from the storage area 300 to the transfer area 305. Any convenient transfer system may be employed to transfer the micro-titer array 302 to the next station 306. At the station 306 a robotic arm 308 is under the control of subsystem controller 309, which communicates with master controller 304. The robotic arm 308 using micropipette tips 310 transfers microliter quantities of liquid from the microtiter well array 302 to one or more appropriate jet to-be-filled 312 located at a maintenance and fill station 314 under the control of subsystem controller 315, which communicates with master controller 304. For reusable jetting devices, the maintenance and fill station has maintenance caps 316, which provide conduits for evacuation and pressure, as well as adding the cleaning solvents, as previously described.

A holder 318 positions the jetting device 312 on a translation bar 320. Using the translation bar 320 and the holder 318 for coupling the jetting device 312 to the translation bar 320, the jetting device 312 is moved to the test station 322 under the control of subsystem controller 323. By means of a strobe light 324 and mirror 326, where the strobe light is synchronized to the voltage pulse to the jetting device, the image of the droplets 328 is transmitted to video camera 330, which transmits the signal to monitor 332 for evaluation of the size and frequency of the droplets 328. If the jetting device 312 does not have the correct characteristics, the jetting device 312 is rejected and the information is forwarded to the master controller 304 to provide a substitute jetting device carrying the same liquid medium.

If the jetting device 312 passes the test station, it is then moved by means of the translation bar 320 to the jetting position 334, being positioned over the substrate 336 by means of the translation bar 320 and the holder 318. The jetting dispenser is now in position to begin jetting drops to create the array. The substrate 336 is mounted on platform 337 which is moved by motor 340. The motor 340 is under the control of controller 342, which transmits to and receives signals from the master controller 304.

The computer-based system controls and coordinates the operation of each of the subsystems in order to maximize throughput, as measured by the number of micro-arrays produced per unit time having the correct distribution of spots. Because the master computer only coordinates and does not directly control each subsystem, a microcomputer-based master would function satisfactorily. In producing a large number (hundreds to thousands) of identical arrays, each having 100×100 spots containing potentially 10,000 different components, e.g. cDNA clones. There is, however, an advantage to include 2–3x redundancy in favor of accuracy and reliability. Also, as to the number of individual samples which are spotted in the array.

As illustrative of the system, detection of one or more cDNA sequences will be exemplified. The master receives a list of clones to be spotted. The list is converted to a list of addresses which determines the number and sequence of microtiter plats to be withdrawn from storage. The conveyer extracts each plate in succession and presents the plate to the location for micropipette transfer. After thawing or warming the sample, as needed, the micropipette robotic transfers a small amount of sample to an available (cleaned or new) jetting device. The master queries the maintenance/fill station as to the status and availability of jetting devices; in consequence, the master notifies the jet exchange/translation subsystem as to which jets have been filled and are ready for jetting. On the way to the active jetting subsystem, the translation is stopped at the jetting test station for confirmation that the device is working properly. Adjacent to the active jetting subsystem, the jet is coupled to the positioner. The positioner places the device at about 100–200µ from the surface at an appropriate angle, and electrically connects the jet to the subsystem controller. The master informs the subsystem as to each jet the address locations on each of the arrays to be formed on the substrate. The subsystem controller then determines the optimal jetting path. On completion of jetting, the used jetting device is disposed of or returned to the maintenance/fill station for cleaning and refilling.

As already described, the active jetting may take place in one of several modes. The preferred modes are a) moving the jet in an x-y plane over a stationary substrate; and b) rotating disk substrate with the jet moving in a single dimension. The master controller provides the jetting subsystem with the addresses for the locations to be spotted on each array.

To carry out the process, a number of steps are performed to prepare the capillary for pulse jetting. Where a capillary has been used previously, cleaning will be necessary to prevent contamination. The pulse jetting device may have the capillary dipped into a cleaning solution and by means of a vacuum, the cleaning solution drawn up into the capillary extending into the receptacle. After sufficient time, the cleaning solution may be blown out of the capillary. Various solutions may be used, depending upon the nature of the sample. Volatile polar organic solvents find particular use, although in some instances, one may use repeated rinses with different cleaning solutions, such as a detergent containing aqueous solution, mildly acidic or basic solutions, organic solvents, and the like. By applying gas pressure to the capillary, the cleaning solution may be expelled and the cleaning process repeated. By having an elevated pressure gas line, one may use dry air, warmed air, or the like to ensure that the capillary is free of any moisture or other liquid. Once the cleaning solution has evaporated, the sample may be added to the receptacle. Generally, the sample will have a volume of about 10 to 100 microliters. The droplet upon touching the upper surface of the capillary is drawn into the capillary by capillary action, completely filling the capillary, while a small portion of the droplet may remain in the receptacle. In some instances, where liquid does not contact the capillary immediately, a small pressure pulse of short duration may conveniently be employed to achieve contact. The pulse jetting device is now ready for use for delivering droplets. The jetting device may be used in a vertical position, directing the droplets upwardly or downwardly or directing the droplets in a horizontal line at the axis of the capillary.

By using jets formed in arrays, tremendous time savings can be achieved, which allow for the production of large numbers of spot arrays, each spot array having a large number of individual spots in a predesigned distribution. For example, suppose one wished to produce a set of 400 "chips," each containing 100×100 element arrays to be formed from 2500 different sample or reagent solutions (e.g. DNA or RNA fragments or oligonucleotides) at a redundancy of 4. The distribution would be to have the redundant spots on different lines both horizontally and vertically. The chip size is set at 2 cm×2 cm, each containing a 1 cm×1 cm array (spot-to-spot distance is 100 microns.) The active jetting area is square, 40 cm×40 cm (i.e. 20×20 chips). The jetting over the active area is achieved using an X-Y Cartesian motion (mastering) of the jet relative to the surface to be spotted. The speed of the jet relative to the array is 50 cm/sec. (Ramp-to-speed times are not included in these calculations; the total scan times would increase about 10–20% if included.) Jetting is performed "on the fly," in the sense that the jet devices are moving as the droplets are dispensed from the jet devices.

The jetting time for a single jet is as follows:
  # horizontal scan lines:
    4 lines/chip×20 chips vertically=80 lines (assumes redundant spots on 4 different lines)
  # cm distance for horizontal and vertical scans:
    40 cm/line×80 lines=3200 cm, horizontally.
    40 cm/line×2 lines (1 up and 1 down)=80 cm, vertically.
  # cm total scan distance: 3280 cm.
  Scan time: 50 cm/sec×3280 cm=164,000 sec, or almost 114 hrs.

By using a linear array of 10 jets with jets aligned horizontally, there is a 10-fold reduction in time to below 12 hrs, with a further time reduction obtained by reduced jet-exchange time. During the scan, one can be firing and filling jets in a continuous manner to provide the necessary diversity and array size in a reasonable time frame.

A jetting device was constructed, employing a capillary tube having a 45 micron orifice at the jetting end, a 0.25 mm inner diameter and a 0.75 mm outer diameter. A ceramic tube (PZT-5a) was attached near the orifice end by epoxy adhesive. The capillary tube was supported by a brass threaded rod and held in place with epoxy adhesive. The main housing (brass) was threaded over the free end of the capillary allowing the end of the capillary to protrude through a small hole. A small groove in the threaded rod, in conjunction with a small notched collar provided a port for the transducer wires. A threaded tube (brass) was threaded onto the threaded rod to hold the notched collar in place. A threaded nylon adaptor having a conically shaped hole was threaded into the "feed" end of the assembly.

The non-wetting conically shaped internal structure of the nylon adapter was designed for convenient loading of sample. As small quantities (10–50 $\mu$L) of aqueous solutions are transferred by micropipet, a combination of gravity and/or other forces directs the small droplet to the bottom of the cone opening adjacent to the capillary tube. The hole diameter of the nylon adapter is the same as the outer diameter of the capillary tubing (approximately 0.25 mm). As the glass at the end of the capillary is wetted, the entire capillary fills rapidly with fluid by means of capillary action, including the region of the orifice. No further priming is necessary for producing droplets.

The driver voltage will generally be in the range of about 0 to 300V, with a pulse duration in the range of about 5 to 150 $\mu$sec. The repetition rate will be in the range of up to about 10,000/sec. Fluids that can be accommodate without external heat will have viscosities in the range of about 0.1 to 1000 mPas, while with a heater, the viscosity can be 20,000 mPas or greater.

A typical voltage pulse with an aqueous medium is bipolar, 80 microseconds long, of equal duration of about 100 V, with rise and fall times of about 10 microseconds. The pulse shape and amplitude is controlled by computer, and can be varied in order to form well-shaped microdrops with minimal satellite droplet formation.

The piezoelectric jetting device can be fired repeatedly at several hundred or thousand pulses/sec, 10,000 Hz or more, so long as there is liquid in the capillary above the transducer. Similarly, the bubble jet can fire at greater than 1000 pulses/sec.

Using the piezoelectric jetting device described above, fluids that were tested in the pulse jetting device and found to jet satisfactorily included water, and buffered DNA solutions (1–100 $\mu$g/mL). The DNA solutions were jetted onto standard glass microscope slides coated with polylysine, which enhances DNA binding to the surface, forming 10×10 arrays or larger of DNA spots having 80–100 micron spacing between centers with spacing of about 20 microns between edges. The DNA was labeled with fluorescein, thus allowing the DNA arrayed slides to be visualized using a fluorescent scanner (15 micron resolution). In addition to nucleic acid solutions, protein solutions, subcellular entities and cells, molecular aggregations, and the like, may also be employed. The media may be organic or inorganic, or combinations thereof, such as aqueous media, alcohols, ethers, saline solutions, polar organic solvents, oils, mercury, and the like.

A computer program may be provided which controls the use of the subject jetting devices. Various programs may be readily devised which provide for the cleaning and filling of the jetting devices, the movement of the devices in relation to the substrate and the firing of the devices to provide the desired arrays. The particular control mechanism is not critical and will be devised in accordance with the needs of the system. The sophistication of the system will depend upon the number of jetting devices to be employed, the complexity of the array pattern, the number of different samples and reagents, and the like.

The subject pulse jetting devices are particularly convenient in providing for sample dispensing into a receptacle above the capillary. Thus, the capillary need not be introduced into a sample, where the capillary could contaminate the sample or become clogged in the event that there is particulate matter in the sample. Therefore, by dispensing sample from above at the top of the capillary, rather than sipping, a more versatile device less likely to result in breakdown is obtained. The subject devices are readily prepared, are rugged, and can be readily machined and produced to provide pulse jetting accurately. The capillaries can be formed with a variety of sized orifices so as to control the size of the spot which is formed. The orifice can respond to the nature of the sample, varying the size with the viscosity and surface tension of the sample solution. In addition, large numbers of the pulse jetting devices can be reproduced, so as to give accurate, repetitive dispensing of droplets.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A system for creating microsized spots using microsized droplets from jetting dispensers so as to produce an array, said system comprising:

a storage station, a maintenance and fill station, a test station and a jetting station;

said storage station comprising means for storing different identified samples in individual containers;

recording means for recording the identity of the sample in each container;

means for relocating said sample containers in accordance with the compositions of said droplets to be dispensed from said storage station to said maintenance and filling station;

said maintenance and filling station comprising a plurality of jetting devices selected from the group consisting of piezoelectric dispensers and thermal dispensers, holders for each of said jetting devices, a moving means for moving said jetting devices in said holders to said test station, and means for filling said jetting devices with identified samples;

said test station comprising means for monitoring the frequency and stability of droplets dispensed from said jetting devices;

means for transporting said jetting device from said test station to said jetting station and positioning said jetting device;

means for moving at least one of said jetting device or a substrate in relation to one another; and means connected to each of said stations for monitoring the filling, moving and jetting of said jetting devices.

2. A system according to claim 1, wherein said jetting devices comprise capillaries and wherein the means for filling includes means for filling the capillaries from the top by capillary action.

3. A system according to claim 1, wherein said moving means comprises a circular platform for supporting said substrate and a motor for controlling the rotation of said platform.

4. A system according to claim 1, wherein said moving means comprises servomechanisms for moving said jetting devices in an x-y direction relative to said substrate.

5. A system according to claim 1, wherein a plurality of jetting devices are held together to move as a group relative to said substrate.

6. A system according to claim 1, wherein each thermal dispenser comprises:

a housing comprising a first constricted opening at one end and a second opening at the other end, a heater channel comprising a nozzle extending through said first opening;

a heating element proximal to said nozzle in said heater channel;

a sample receptacle in liquid transfer relationship with said second end and extending into said housing, wherein the composition of said sample receptacle and heater channel are selected so that upon contact of said sample with said heater channel, said sample fills said heater channel by capillary action; and means for connecting said heating element to a control system, whereby droplets capable of providing arrays of spots less than 500 microns from center to center with substantially no contamination of one spot with another are obtained.

7. A system according to claim 6, wherein said sample receptacle has a volume ranging from about 0.2 to 20 microliters.

8. A system according to claim 6, wherein said heater channel is hydrophilic and said receptacle is hydrophobic.

9. A system according to claim 1, wherein each piezoelectric dispenser comprises:

a housing comprising a first constricted opening at one end and a second opening at the other end;

a capillary comprising a dispensing orifice having a diameter in the range of about 10 to 100 microns and a volume capacity in the range of about 1 to 10 microliters and extending a portion of the length of said housing with said dispensing orifice extending through said first opening;

proximal to said dispensing orifice, a piezoelectric transducer mounted concentrically on said capillary and affixed to said capillary, wherein the walls of said capillary move with the movement of said transducer;

proximal to said second end and extending at least about 40% of the length of said capillary a capillary casing affixed to said capillary, with said casing filling the space between said capillary and the inner wall of said housing;

in liquid transfer relationship with said second end and extending into said housing, a sample receptacle, wherein the composition of said receptacle and capillary are selected so that upon contact of said sample with said capillary, said sample fills said capillary by capillary action; and means for connecting said piezoelectric transducer to a control system; whereby droplets capable of providing arrays of spots of less that 500 microns from center to center with substantially no contamination of one spot with another are obtained.

10. A system according to claim 9, wherein said capillary has walls of from 0.10 to 0.40 mm in thickness.

11. A system according to claim 9, wherein said sample receptacle has volume ranging from about 5 to 50 microliters.

12. A system according to claim 9, wherein said capillary is hydrophilic and said receptacle is hydrophobic.

13. A system according to claim 12, wherein said capillary is glass and said receptacle is nylon.

14. A system according to claim 9, wherein said device further comprises a lid having a plurality of conduits, each conduit being valved, and means for hermetically sealing said lid to said receptacle.

* * * * *